(12) United States Patent
Mathies et al.

(10) Patent No.: US 7,438,792 B2
(45) Date of Patent: Oct. 21, 2008

(54) SEPARATION SYSTEM WITH A SHEATH-FLOW SUPPORTED ELECTROCHEMICAL DETECTOR

(75) Inventors: Richard A. Mathies, Moraga, CA (US); Charles A. Emrich, Berkeley, CA (US); Pankaj Singhal, Pasadena, CA (US); Peter Ertl, Styria (AT)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 11/107,295

(22) Filed: Apr. 14, 2005

(65) Prior Publication Data
US 2005/0230254 A1    Oct. 20, 2005

Related U.S. Application Data

(60) Provisional application No. 60/563,917, filed on Apr. 20, 2004.

(51) Int. Cl.
G01N 27/447    (2006.01)
G01N 27/453    (2006.01)

(52) U.S. Cl. .................... 204/452; 204/409; 204/603

(58) Field of Classification Search ............... 204/452, 204/454, 600, 603, 601, 409
See application file for complete search history.

(56) References Cited

U.S. PATENT DOCUMENTS 6,090,251 A * 7/2000 Sundberg et al. .......... 204/453
6,143,152 A * 11/2000 Simpson et al. ............ 204/451
6,361,671 B1   3/2002 Mathies et al.
7,108,775 B2 * 9/2006 Bahatt et al. .............. 204/601
2004/0043506 A1 * 3/2004 Haussecker et al. ........ 436/180

OTHER PUBLICATIONS

Haab et al, Analytical Chemistry, 1999, 71, pp. 5137-5145.*
Manz et al, J. Micromech. Microeng. 4 (1994) pp. 257-265.*
Scott Martin et al, Analytical Chemistry 2002, 74, pp. 1136-1143.*
Manz, A.; Graber, N.; Widmer, H. M., "Miniaturized Total Chemical Analysis Systems: a Novel Concept For Chemical Sensing", Sens. Actuator B-Chem. 1990, 1, 244-248.
Reyes, D. R.; Iossifidis, D.; Auroux, P. A.; Manz, A., "Micro Total Analysis Systems. 1. Introduction, Theory, and Technology", Anal. Chem. 2002, 74, 2623-2636.
Figeys, D.; Pinto, D., "Lab-on-a-Chip: A Revolution in Biological and Medical Sciences", Anal. Chem. 2000, 72, 330A-335A.
Paegel, B. M.; Yeung, S. H. I.; Mathies, R. A., "Microchip Bioprocessor For Integrated Nanovolume Sample Purification and DNA Sequencing", Anal. Chem. 2002, 74, 5092-5098.
Auroux, P. A.; Iossifidis, D.; Reyes, D. R.; Manz, A., "Micro Total Analysis Systems. 2. Analytical Standard operations and Applications", Anal. Chem. 2002, 74, 2637-2652.

(Continued)

Primary Examiner—Kaj K Olsen
(74) Attorney, Agent, or Firm—Weaver Austin; Villeneuve & Sampson LLP

(57) ABSTRACT

An electrochemical detector including side channels associated with a separation channel of a sample component separation apparatus is provided. The side channels of the detector, in one configuration, provide a sheath-flow for an analyte exiting the separation channel which directs the analyte to the electrically developed electrochemical detector.

29 Claims, 13 Drawing Sheets

OTHER PUBLICATIONS

Vandaveer, W. R.; Pasas, S. A.; Martin, R. S.; Lunte, S. M., "Recent Developments in Amperometric Detection For Microchip Capillary Electrophoresis", *Electrophoresis* 2002, 23, 3667-3677.

Brazill, S. A.; Kuhr, W. G., "A Single Base Extension Technique For The Analysis of Known Mutations Utilizing Capillary Gel Electrophoresis With Electrochemical Detection", *Anal. Chem.* 2002, 74, 3421-3428.

Brazill, S. A.; Kim, P. H.; Kuhr, W. G., "Capillary Gel Electrophoresis With Sinusoidal Voltammetric Detection: A Strategy To Allow Four-"Color" DNA Sequencing", *Anal. Chem.* 2001, 73, 4882-4890.

Lacher, N. A.; Garrison, K. E.; Martin, R. S.; Lunte, S. M., "Microchip Capillary Electrophoresis/electrochemistry", *Electrophoresis* 2001, 22, 2526-2536.

Baldwin, R. P., "Recent Advances in Electrochemical Detection In Capillary Electrophoresis", *Electrophoresis* 2000, 21, 4017-4028.

Wang, J.; Polsky, R.; Tian, B. M.; Chatrathi, M. P., "Voltammetry on Microfluidic Chip Platforms", *Anal. Chem.* 2000, 72, 5285-5289.

Tanyanyiwa, J.; Leuthardt, S.; Hauser, P. C., "Conductimetric and Potentiometric Detection in Conventional and Microchip Capillary Electrophoresis", *Electrophoresis* 2002, 23, 3659-3666.

Gavin, P. F.; Ewing, A. G., "Continuous Separations With Microfabricated Electrophoresis—Electrochemical Array Detection", *J. Am. Chem. Soc.* 1996, 118, 8932-8936.

Woolley, A. T.; Lao, K. Q.; Glazer, A. N.; Mathies, R. A., "Capillary Electrophoresis Chips With Integrated Electrochemical Detection", *Anal. Chem.* 1998, 70, 684-688.

Wang, J.; Tian, B. M.; Sahlin, E., "Integrated Electrophoresis Chips/Amperometric Detection With Sputtered Gold Working Electrodes", *Anal. Chem.* 1999, 71, 3901-3904.

Rossier, J. S.; Roberts, M. A.; Ferrigno, R.; Girault, H. H., "Electrochemical Detection in Polymer Microchannels", *Anal. Chem.* 1999, 71, 4294-4299.

Schwarz, M. A.; Hauser, P. C., "Recent Developments in Detection Methods For Microfabricated Analytical Devices", *Lab Chip* 2001, 1, 1-6.

Holland, L. A.; Leigh, A. M., "Amperometric and Voltammetric Detection For Capillary Electrophoresis", *Electrophoresis* 2002, 23, 3649-3658.

Wang, J.; Chatrathi, M. P.; Tian, B. M., Micromachined Separation Chips With A Precolumn Reactor and End-Column Electrochemical Detector:, *Anal. Chem*, 2000, 72, 5774-5778.

Martin, R. S.; Ratzlaff, K. L.; Huynh, B. H.; Lunte, S. M., In-Channel Electrochemical Detection For Microchip Capillary Electrophoresis using an Electrically Isolated Potentiostat:, *Anal. Chem.* 2002, 74, 1136-1143.

Chen, D. C.; Hsu, F. L.; Zhan, D. Z.; Chen, C. H., "Palladium Film Decoupler For Amperometric Detection in Electrophoresis Chips", *Anal. Chem.* 2001, 73, 758-762.

Rossier, J. S.; Ferrigno, R.; Girault, H. H., "Electrophoresis With Electrochemical Detection in a Polymer Microdevice", *J. Electroanal. Chem.* 2000, 492, 15-22.

Wallenborg, S. R.; Nyholm, L.; Lunte, C. E., "End-Column Amperometric Detection in Capillary Electrophoresis: Influence of Separation-Related Parameters on the Observed Half-Wave Potential For Dopamine and Catechol", *Anal. Chem.* 1999, 71, 544-549.

Klett, O.; Bjorefors, F.; Nyholm, L., "Elimination of High-Voltage Field Effects in End Column Electrochemical Detection in Capillary Electrophoresis by Use of On-Chip Microband Electrodes", *Anal. Chem.* 2001, 73, 1909-1915.

Hirschhornn, J. N.; Sklar, P.; Lindblad-Toh, K.; Lim, Y. M.; Ruiz-Gutierrez, M.; Bolk, S.; Langhorst, B.; Schaffner, S.; Winchester, E.; Lander, E. S., "SBE-TAGS: An Array-Based Method For Efficient Single-Nucleotide Polymorphism Genotyping", *Proc. Natl. Acad. Sci. U. S. A.* 2000, 97, 12164-12169.

Yang, I. V.; Ropp, P. A.; Thorp, H. H., " Toward Electrochemical Resolution of Two Genes on One Electrode: Using 7-Deaza Analogues of Guanine and Adenine To Prepare PCR Products with Differential Redox Activity", *Anal. Chem.* 2002, 74, 347-354.

Yu, C. J.; Wan, Y. J.; Yowanto, H.; Li, J.; Tao, C. L.; James, M. D.; Tan, C. L.; Blackburn, G. F.; Meade, T. J., "Electronic Detection of Single-Based Mismatches in DNA With Ferrocene-Modified Probes", *J. Am. Chem. Soc.* 2001, 123, 11155-11161.

Feder, J. N., et al., "A Novel MHC Class I-like Gene is Mutated In Patients With Hereditary Haemochromatosis", *Nat. Genet.* 1996, 13, 399-408.

Lagally, E. T.; Emrich, C. A.; Mathies, R. A., Fully Integrated PCR-capillary Electrophoresis Microsystem For DNA Analysis, *Lab Chip* 2001, 1, 102-107.

Takenaka, S.; Uto, Y.; Kondo, H.; Ihara, T.; Takagi, M., "Electrochemically Active DNA Probes: Detection Target DNA Sequences at Femtomole Level by High-Performance Liquid Chromatography With Electrochemical Detection", *Anal. Biochem.* 1994, 218, 436-443.

Anne, A.; Blanc, B.; Moiroux, J., "Synthesis of the First Ferrocene-Labeled Dideoxynucleotide and its Use for 3'-Redox End-Labeling of 5'-Modified Single-Stranded Oligonucleotides", *Bioconjugate Chem.* 2001, 12, 396-405.

Medintz, I.; Wong, W. W.; Sensabaugh, G.; Mathies, R. A., High Speed Single Nucleotode Polymorphism Typing of a Hereditary Haemochromatosis Mutation With Capillary Array Electrophoresis Microplates, *Electrophoresis* 2000, 21, 2352-2358.

Baldwin, R. P.; Roussel, T. J.; Crain, M. M.; Bathlagunda, V.; Jackson, D. J.; Gullapalli, J.; Conklin, J. A.; Pai, R.; Naber, J. F.; Walsh, K. M.; Keynton, R. S., "Fully Integrated On-Chip Electrochemical Detection For Capillary Electrophoresis in a Microfabricated Device", *Anal. Chem.* 2002, 74, 3690-3697.

Martin, R. S.; Gawron, A. J.; Lunte, S. M.; Henry, C. S., "Dual-Electrode Electrochemical Detection For Poly(dimethylsiloxane)-Febricated Capillary Electrophoresis Microchips", *Anal. Chem.* 2000, 72, 3196-3202.

Schwarz, M. A.; Galliker, B.; Fluri, K.; Kappes, T.; Hauser, P. C., "A Two-Electrode Configuration For Simplified Amperometric Detection in a Microfabricated Electrophoretic Separation Device", *Analyst* 2001, 126, 147-151.

Emrich, C.A., Ertl, P., Singhal, P., Mathies, R.A., "Capillary Electrophoresis by Use of On-Chips With a Sheath-Flow Supported Electrochemical Detection System", *Anal. Chem.* 76, 3749-3755 (2004).

\* cited by examiner

SEPARATION SYSTEM WITH A SHEATH-FLOW SUPPORTED ELECTROCHEMICAL DETECTOR

CROSS REFERENCE TO RELATED APPLICATIONS

This application claims priority under 35 U.S.C. 119(e) from Provisional U.S. Patent Application Ser. No. 60/563,917, filed Apr. 20, 2004, entitled "MICROFABRICATED SEPARATION SYSTEM WITH AN INTEGRATED SHEATH-FLOW-SUPPORTED ELECTROCHEMICAL DETECTOR", which is incorporated herein by reference.

STATEMENT REGARDING FEDERALLY SPONSORED RESEARCH

The techniques and mechanisms of the present invention were made with Government support under NIH Grant No. HG01399 and Department of Energy Grant No. FG03-91ER61125.

BACKGROUND

1. Field of Invention

The present invention relates to chemical analysis systems and techniques. In one example, the present invention relates to methods and apparatus for providing microfluidic electrochemical detection systems with increased sensitivity and reliability.

2. Description of Related Art

The miniaturization of chemical and biochemical analysis instrumentation has enabled the widespread use of such instrumentation in high-throughput and point-of-care applications. High-speed electrophoretic separations of biomolecules are now routinely performed in micron-sized capillaries and have been proven on microfabricated capillary electrophoresis (CE) devices. These techniques offer a significant increase in speed over previous techniques. However, the fluorescence-based detection methods often employed require large and expensive optical detection systems. Significant cost and space savings can be achieved by using electrochemical (EC) methods for detection.

Microfabricated devices are ideally suited to EC detection of biomolecules because of the relative ease of integration of the metallic components required for the detection electrodes. Although conductimetry, voltammetry, and potentiometry have all been employed in CE-EC systems, amperometry is the most widely used EC detection technique for chip-based separations. An important issue when performing amperometric detection with CE is the necessary electrical isolation of the EC detector from the separation voltage, since interference from the CE current significantly influences detector performance. The need to isolate or decouple the CE and EC systems arises from the fact that the separation voltages used in CE typically generate $\mu A$-level background EC currents, masking the pA to nA currents measured at the working electrode of an EC detection system. Therefore, for optimum CE-EC performance, the electrical overlap of the two systems must be controlled and minimized.

Several approaches have been developed to minimize the influence of CE fields, including end-channel detection on chip, end-channel detection off-chip, in-channel detection and off-channel detection. In- and off-channel detection involve the placement of the working electrode directly within the separation channel using either an electrically isolated "floating" potentiostat or electric-field decouplers. End-channel (or end-column) detection is the most commonly used mode of amperometric detection, where the working electrode is placed close to, for example, 10 to 50 microns ($\mu m$), the exit of the separation channel. The majority of the CE voltage is dropped along the high-resistance capillary or separation channel (inside diameter, for example, approximately 25 $\mu m$) resulting in very little of it being dropped in the low-resistance detection reservoir, minimizing current in the detector region. However, since the grounded-end of the CE circuit is within the detection reservoir, the remaining electric field causes potential shifts at the working electrode of the detector. In general, end-channel detection exhibits high background currents and separation efficiency is sacrificed due to diffusion of the analyte in the region between the separation channel end and the working electrode of the EC detector.

Therefore, it is desirable to reduce background currents and increase the sensitivity of EC detectors. It is also desirable to enhance the separation efficiency of CE systems.

SUMMARY

In one aspect, the invention features an electrochemical detector. The detector comprises first and second channels located on first and second sides of a separation channel of a sample component separation apparatus. The first and second channels are in fluid communication with an exit end of the separation channel. The first and second channels are configured and arranged to provide a sheath flow at the juncture of the first and second channels with the exit end of the separation channel.

Various implementations of the invention may include one or more of the following features. The separation channel is configured to perform an electrophoretic separation. The first side is one lateral side of the separation channel and the second side is an opposite lateral side of the separation channel. The first side is an upper surface of the separation channel and the second side is a lower surface of the separation channel. The first and second channels are arranged at an angle greater than 0° but less than or equal to 90° relative to the separation channel. The flow from the first and second channels controls the lateral and vertical direction of movement of a sample component exiting the separation channel.

The fluid may be introduced into the first and second channels by a gravity driven flow, a pressure-generating pump driven flow, or an electroosomotic driven flow. The detector may include a first reservoir for introducing a fluid into the first channel and a second reservoir for introducing a fluid into the second channel. The flow in the first and second channels can be varied to direct a sample component in different directions as it exists the separation channel.

The detector can include a first working electrode and a reference electrode located in an anode reservoir of the sample component separation apparatus. The first working electrode may be located at a distance of between about 100 and 250 microns from the exit end of the separation channel. The first and second channels provide for the hydrodynamic transport of a sample component to the first working electrode and the reference electrode. A sheath flow from the first and second channels transports the sample component to the first working electrode and the reference electrode. The anode reservoir also includes a third electrode that may function either as a working electrode or a reference electrode. The anode reservoir may include a second working electrode to detect a sample component that is different from that detected by the first working electrode. The anode reservoir may include a second working electrode poised at a different potential from that of the first working electrode. The first working electrode detects a first electroactive agent and the second working electrode detects a second electroactive agent that is different from the first electroactive agent. The first working electrode is spaced from the reference electrode by a distance that is less than the diameter of the separation channel. The first and second channels extend substantially parallel to the separation channel and are fluidically connected to another channel that directs the fluidic stream over a working electrode and a reference electrode.

In another aspect, the present invention is directed to an electrochemical detector including first and second channel means in fluid communication with an exit end of a separation channel of a sample component separation apparatus. The first and second channel means provide a sheath-flow at the juncture of the first and second channels with the exit end of the separation channel.

In yet another aspect, the invention features a sample component separation and detector apparatus. The apparatus comprises a cathode reservoir and an anode reservoir. The apparatus also includes a separation channel having an exit end, and the separation channel defines between the cathode reservoir and the anode reservoir a sample transport path. The apparatus further includes a first channel located on a first side of the separation channel and in fluid communication with the separation channel at the exit end. The apparatus also includes a second channel located on a second side of the separation channel and in fluid communication with the separation channel at the exit end. The first and second channels are configured and arranged to provide a sheath flow at the juncture of the first and second channels with the exit end.

Various implementations of the invention may include one or more of the following features. The separation channel is configured to perform an electrophoretic separation. The apparatus further includes a plurality of separation channels and associated first and second channels. Each separation channel defines between an associated cathode reservoir and an associate anode reservoir a sample transport path. The apparatus may be microfabricated. The apparatus may include a sample reservoir and a waste reservoir coupled to the separation channel.

In still another aspect, the invention is directed to a method of separating a sample by electrophoresis. The method includes depositing a sample into a sample reservoir and ejecting a portion of the sample into a separation channel. A voltage is applied between a cathode reservoir and an anode reservoir so as to drive the sample portion along the separation channel toward an exit end of the separation channel where a sheath flow is provided.

Various implementations of the invention may include one or more of the following features. The sheath flow transports the sample portion toward a working electrode and a reference electrode located in the anode reservoir. The lateral and vertical direction of movement of the sample component is controlled as it leaves the exit end of the separation channel. The sheath flow is controlled to steer the sample portion in a selected direction. The flow rate of the sheath flow may also be controlled.

The invention can include one or more of the following advantages. Electroactive analytes can be transported to an EC detector placed relatively far away from the end of a CE separation column. This provides decoupling of the CE electric field from the EC detector. As such, detector sensitivity is significantly increased while separation efficiency is enhanced. Larger separation channels and higher separation electric fields can also be used. Additionally, the EC detector is reliable and relatively easy to use.

These and other features and advantages of the present invention will be presented in more detail in the following specification of the invention and the accompanying figures, which illustrate, by way of example, the principles of the invention.

BRIEF DESCRIPTION OF DRAWINGS

The invention may best be understood by reference to the following description taken in conjunction with the accompanying drawings that illustrate specific embodiments of the present invention.

DETAILED DESCRIPTION

Reference will now be made in detail to some specific embodiments of the present invention including the best modes contemplated by the inventor for carrying out the invention. Examples of these specific embodiments are illustrated in the accompanying drawings. While the invention is described in conjunction with these specific embodiments, it will be understood that it is not intended to limit the invention to the described embodiments. On the contrary, it is intended to cover alternatives, modifications, and equivalents as may be included within the spirit and scope of the invention as defined by the appended claims.

In the following description, numerous specific details are set forth in order to provide a thorough understanding of the present invention. The present invention may be practiced without some or all of these specific details. In other instances, well known process operations have not been described in detail in order not to unnecessarily obscure the present invention.

Furthermore, techniques and mechanisms of the present invention will sometimes be described in singular form for clarity. However, it should be noted that some embodiments can include multiple iterations of a technique or multiple instantiations of a mechanism unless noted otherwise. For example, a single CE-EC system is used in a variety of contexts. However, it will be appreciated that multiple systems can also be used while remaining within the scope of the present invention unless otherwise noted.

Figure 1:
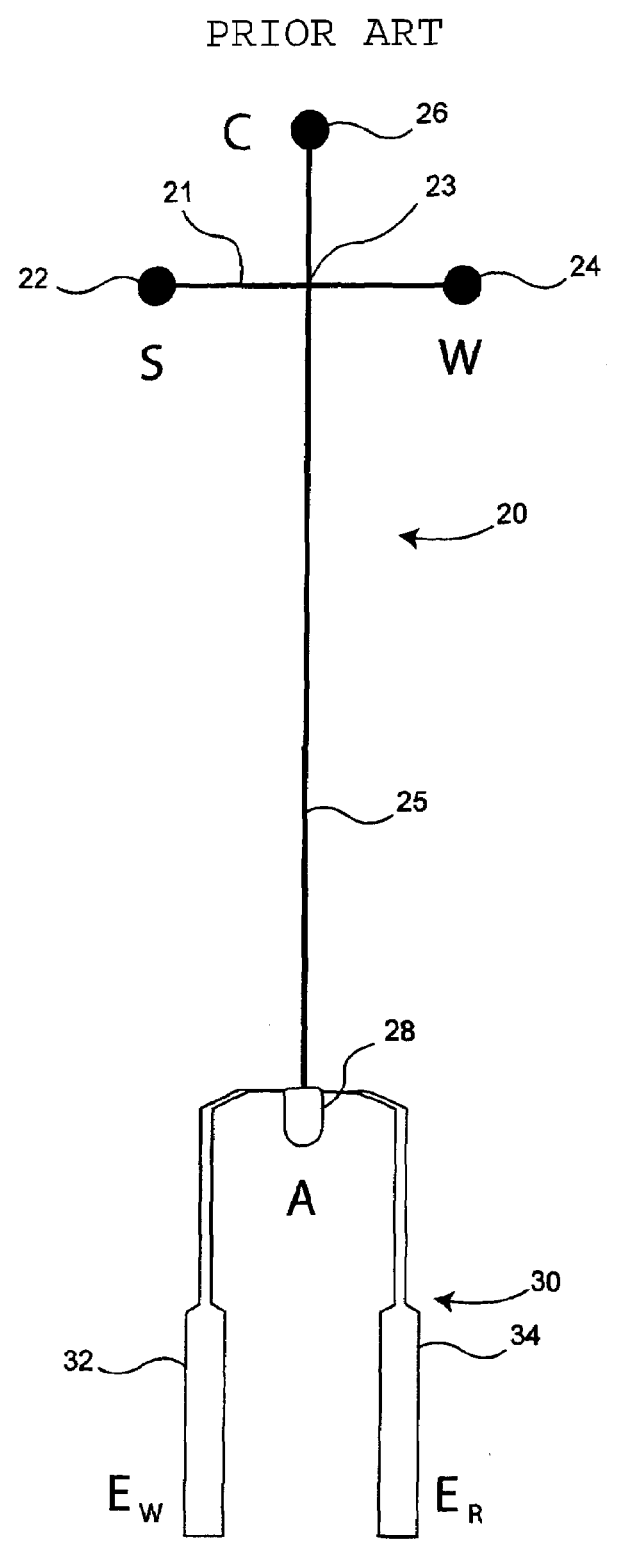
FIG. 1 is a diagrammatic representation of a conventional microfabricated CE-EC system.

As shown in FIG. 1, a conventional microfabricated CE-EC system 20 includes a sample reservoir (S) 22 and a waste reservoir (W) 24. Generally, a sample to be analyzed, that is, an analyte, is injected from the sample reservoir, via an injection channel 21, to the waste reservoir by the application of an electric field. An intersection 23 is formed where the injection channel intersects a separation channel 25. After a predetermined time, the electric field is changed to run from a cathode reservoir (C) 26 to an anode or detection reservoir (A) 28. This carries a small sample amount present at the intersection of channels C-A and S-W (intersection 23) through the separation channel 25 towards the anode reservoir 28. This occurs before detection.

The system 20 further includes an end-column EC detector 30. The detector comprises a working electrode ($E_w$) 32 and a reference electrode ($E_R$) 34. As shown, the working and reference electrodes are placed near to each other and close to the end of the separation channel. Additional electronics, for example, a preamplifier and a potentiostat, are used to perform the measurement of the electrochemical signal. They, however, are not usually included on the microfabricated system.

Figure 2:
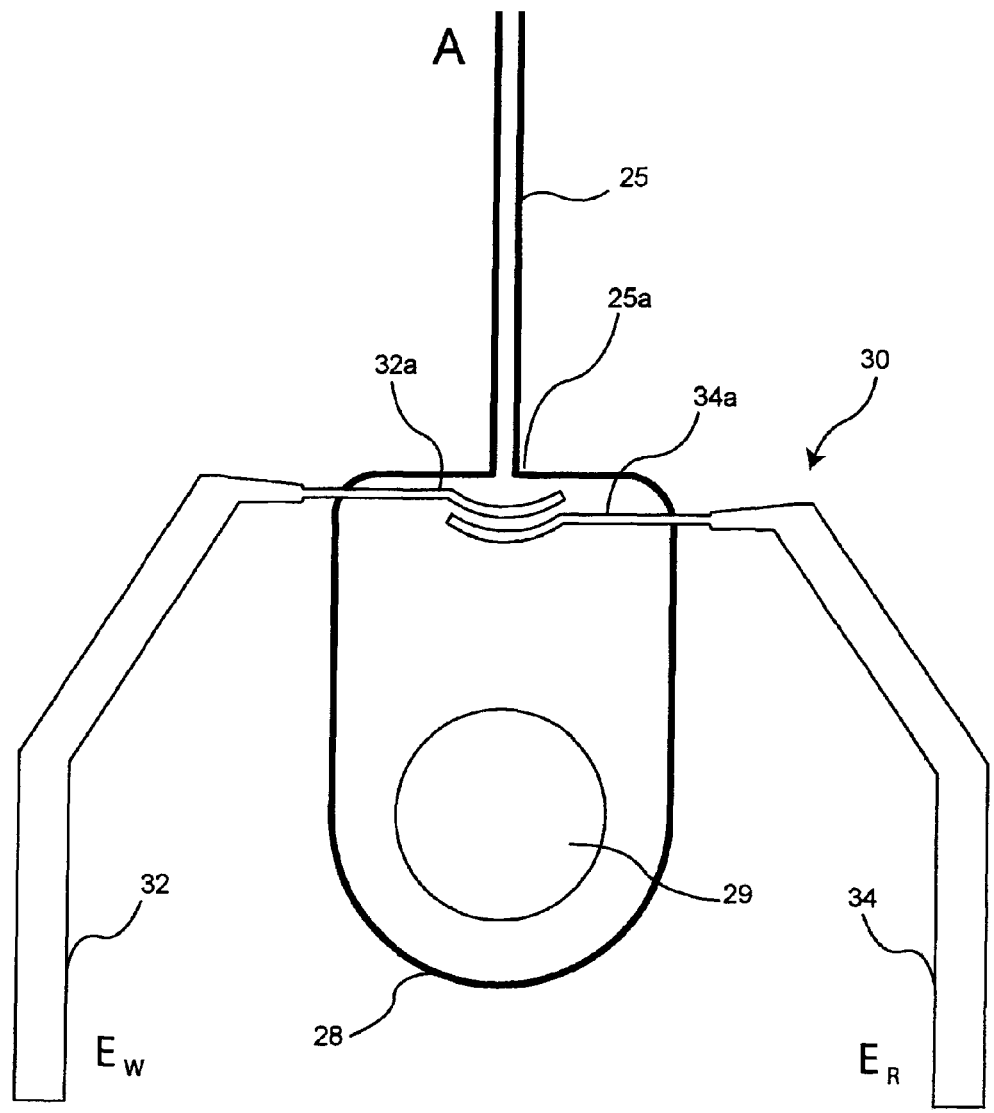
FIG. 2 is a diagrammatic representation depicting the working and reference electrodes, and the detection chamber of the CE-EC system of FIG. 1.

Referring to FIG. 2, during separation, an analyte zone or injection plug (not shown) is driven down the separation channel 25 toward a CE anode 29, following the electrical potential gradient between the CE anode and the CE cathode, which is at the opposite end of the channel 25. Electro-active analytes are detected as they encounter the working electrode 32. The working electrode is held at a fixed or time variable potential vis-a-vis the reference electrode 34.

The position of ends 32a and 34a of the working and reference electrodes, respectively, within the reservoir 28, particularly the distance between them and both separation channel exit 25a and the CE anode 29, have a significant impact on sensitivity and resolution of the detector. As an analyte zone passes from the separation channel 25 to the lower-resistance detection reservoir 28, it will begin to broaden due to diffusion. Because the wider detection reservoir has a lower resistance, the electric field will be concomitantly reduced. As such, the velocity of the analyte zone decreases. Ultimately, the sensitivity of the detector suffers both because the analyte zone has more time to diffuse, and because of the spatial gradient in the electric field as the channel width changes.

Figure 3:
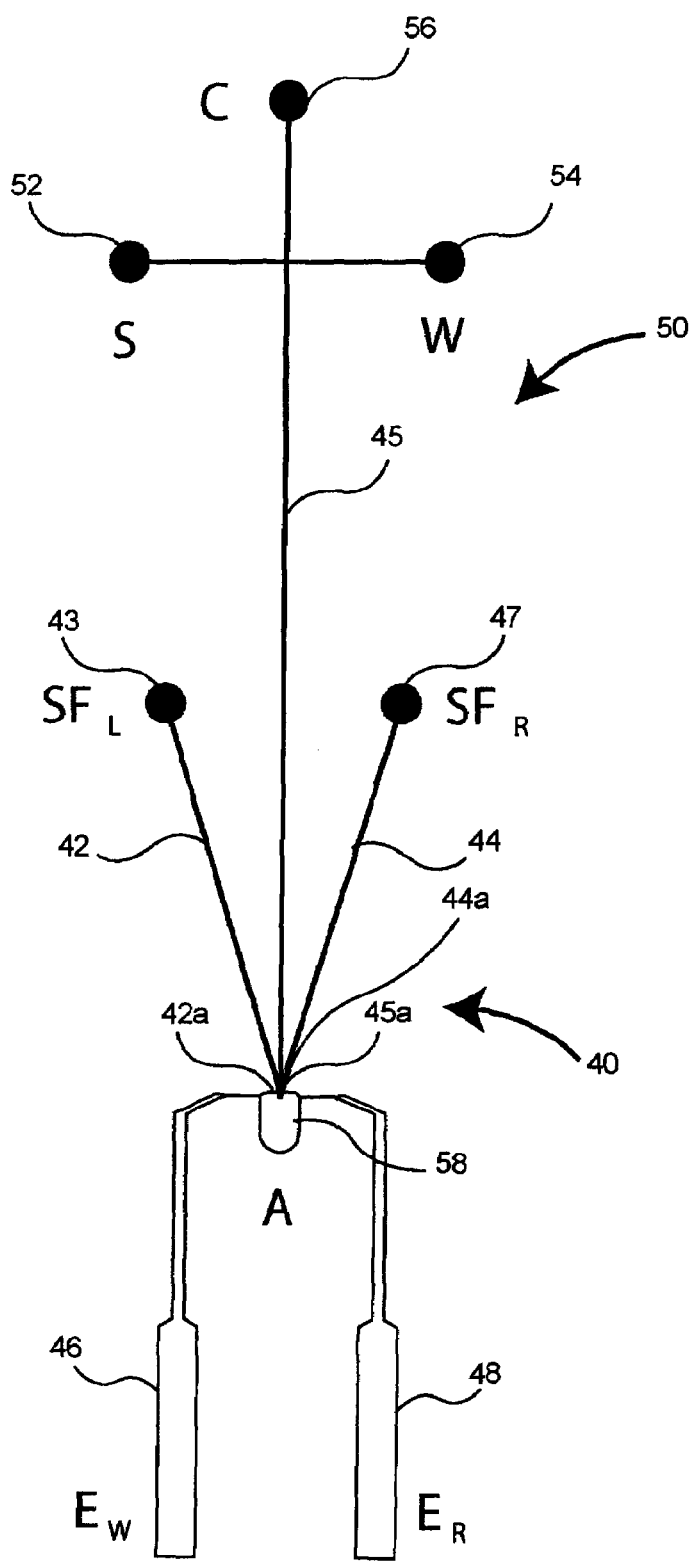
FIG. 3 is a diagrammatic representation of a CE-EC system including side channels in accordance with the present invention.

FIG. 3 is a diagrammatic representation showing an end-column EC detection system 40 that includes channels 42 ($SF_L$) and 44 ($SF_R$). The channels are located on opposite lateral sides of a main separation channel 45 of a sample component separation apparatus, for example, a microfabricated CE device or apparatus 50. Such a CE device, as discussed, includes a sample reservoir (S) 52, a waste reservoir (W) 54, a cathode reservoir (C) 56, and an anode or detection reservoir (A) 58. The detection reservoir includes an anode 59 (see FIG. 4).

Figure 4:
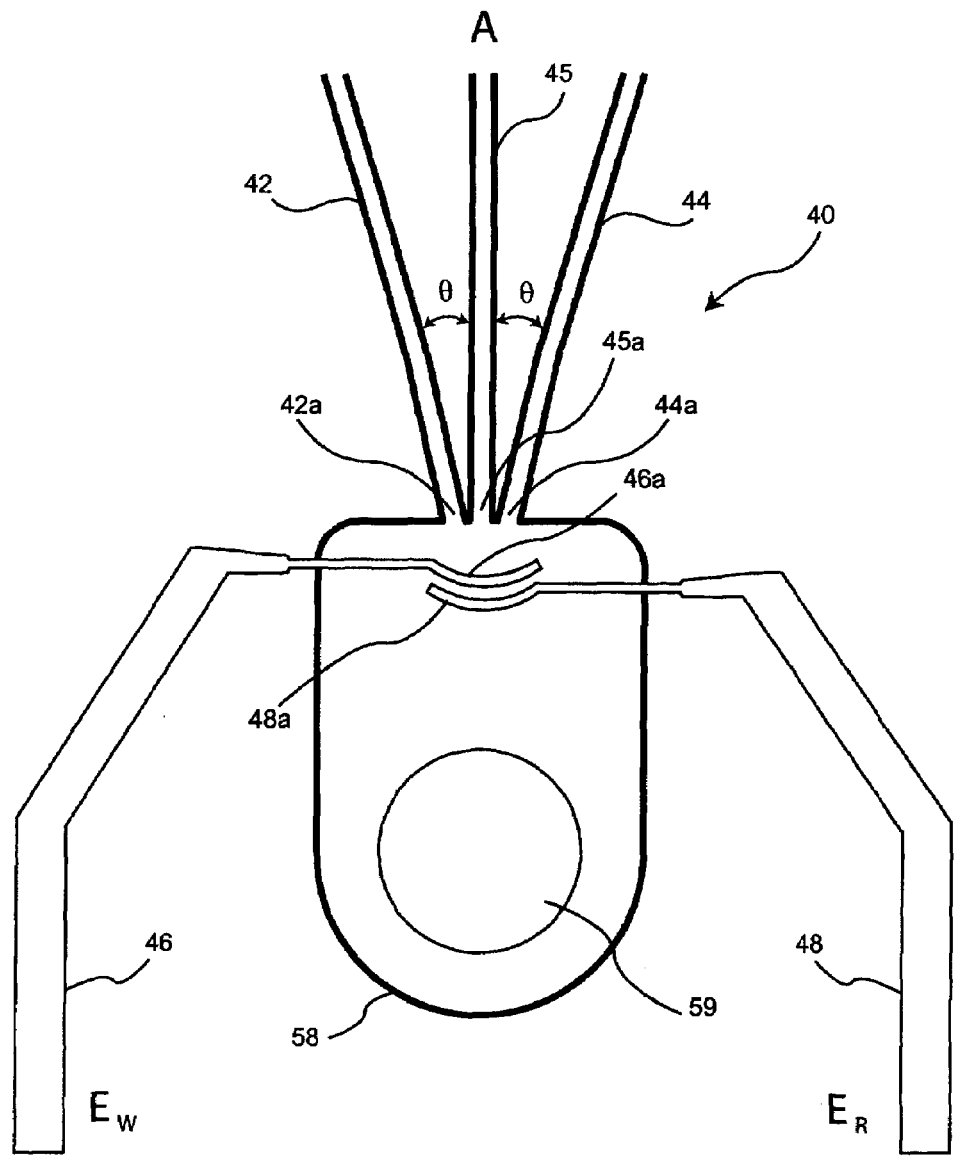
FIG. 4 is a diagrammatic representation of the working and reference electrodes, and the detection chamber of the CE-EC system of FIG. 3.

As shown by FIGS. 3 and 4, the channels 42 and 44 intersect with the detection reservoir 58 adjacent to an exit end 45a of the separation channel 45. As seen from above, the channel 42 is located on the left side of the separation channel, while the channel 44 is on the right side of the separation channel. Each channel 42 and 44 may intersect the separation channel at an angle θ of approximately 30 degrees (°). Alternatively, the side channels may intersect the separation channel at other appropriate angles. For instance, they may intersect the separation channel at an angle greater than 0° but less than or equal to 90°.

The output ends 42a and 44a of the channels 42 and 44, respectively, are located sufficiently close to the exit 45a so as to provide for the hydrodynamic transport of an analyte or analyte zone (not shown) to the detector 40. Specifically, the channels provide a confining sheath flow for the analyte. That is, the flow from the channels substantially surrounds an analyte as it exits the end 45a of the separation column 45. Reservoirs 43 and 47 hold the fluid which is to be introduced into the respective channels.

The presence of the channels 42 and 44 flanking the separation channel 45 ameliorates the dispersion associated with end-column detection. This allows ends 46a and 48a of detection electrodes 46 ($E_w$) and 48 ($E_R$), respectively, to be placed farther from the channel exit 45a, thereby lowering background currents.

Figure 5A:
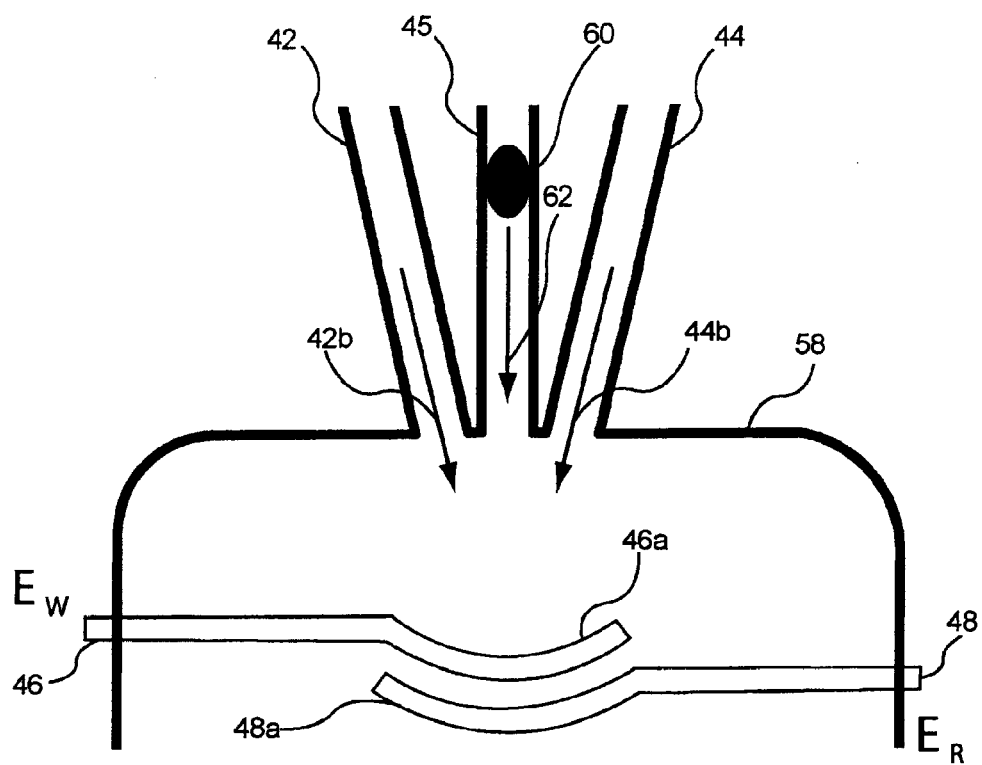
FIGS. 5A and 5B are diagrammatic representations showing a time sequence of operation of an EC detector of the present invention.
Figure 5B:
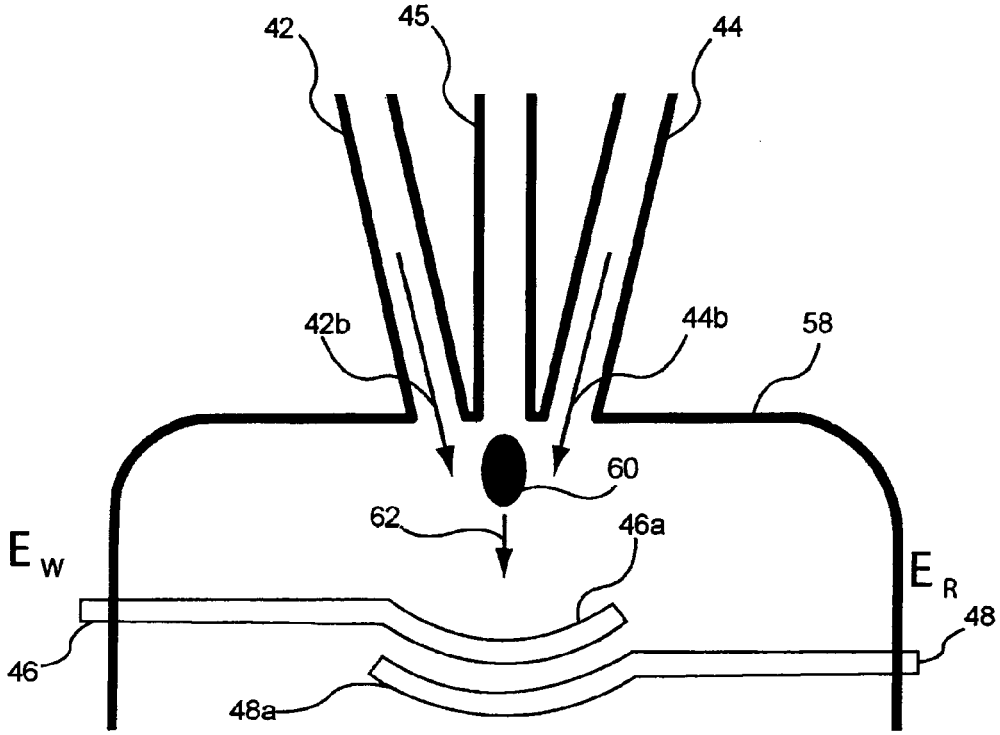

A schematic time sequence of operation of the EC detector system 40 is shown in FIGS. 5A and 5B. An analyte zone 60 (represented by a black ovoid) travels with a velocity, represented by an arrow 62, due to the separation electric field of the CE system. Upon exiting the separation channel end 45a, the velocity due to the electric field is decreased, as shown by FIG. 5B. However, the analyte zone or band 60 then enters the confluent zone where the sheath flow paths 42b and 44b from the channels 42 and 44, respectively, converge. The transport of the analyte zone is then taken over by the sheath flow streams from the channels.

The microfabricated flow channels 42 and 44 may be 5 to 50 μm deep and 10 to 100 μm wide. As such, all flow streams will follow laminar flow models for low Reynolds numbers, that is, Reynolds numbers on the order of below about 1400. This laminar flow behavior will also permit different embodiments of the flow channel arrangements and positions.

Figure 6A:
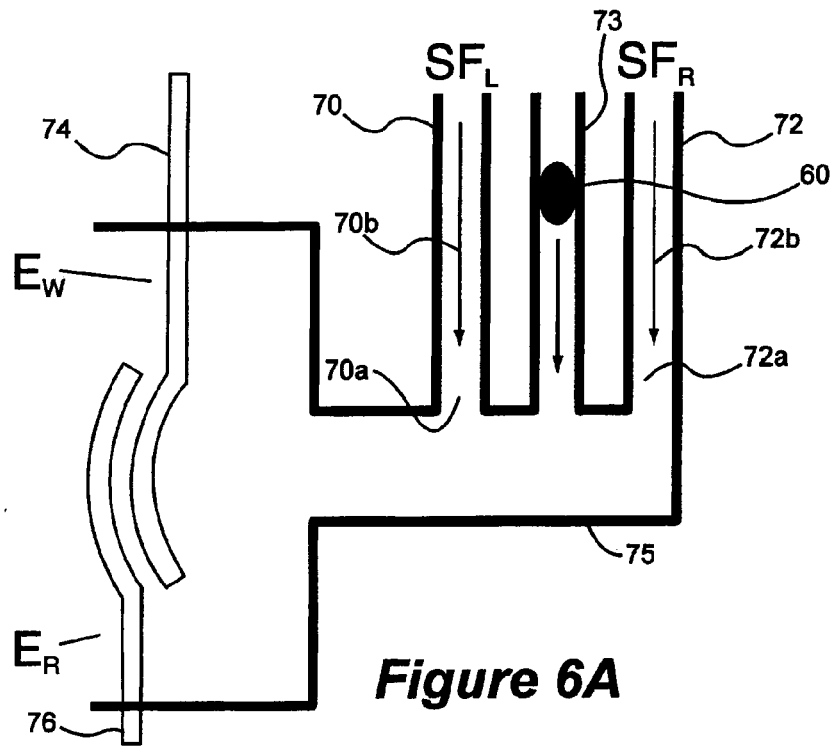
FIGS. 6A and 6B are diagrammatic representations showing alternate embodiments of an EC detector in accordance with the present invention.
Figure 6B:
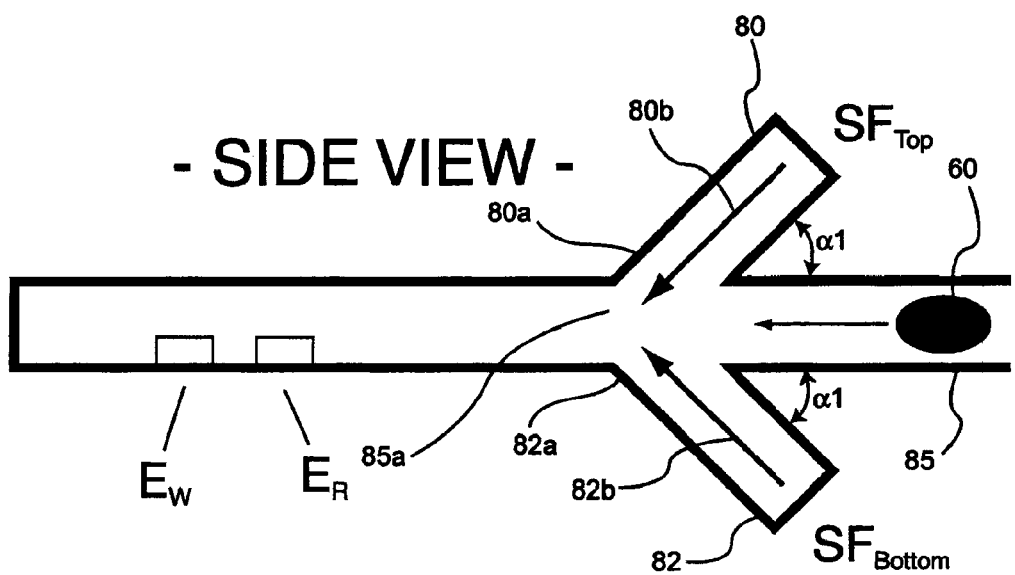

For example, as shown in FIG. 6A, flow channels 70 and 72 extend parallel to a separation channel 73 and are fluidically connected, along with the separation channel 73, to a channel 75. As such, they provide a right angle turn at the channel ends 70a and 72a for their respective fluidic flows 70b and 72b before reaching the detection electrodes 74 and 76 ($E_W$ and $E_R$). Alternatively, as shown in FIG. 6B, flow channels 80 and 82 are configured such that they are routed from vertical planes vis-à-vis a separation channel 85. Specifically, the channel 80 is located above the separation channel, while the channel 82 is located below the separation channel. The channels 80 and 82 may be placed at an angle $\alpha_1$, relative to the separation channel. Like the angle θ, the angle $\alpha_1$ may be approximately 30° or some other appropriate angle. The channels 80 and 82 provide flow control over both the lateral and vertical directions of the analyte zone 60. That is, the flow from the channel ends 80a and 82a (flow paths 80b and 82b) can be directed to control the lateral and vertical direction of movement of the sample component or band 60 as it passes through exit end 85a of the separation channel.

The flow from the channels of the various embodiments of the present invention can be driven by forcing fluid through the channels using various methods. Suitable methods or techniques include, for example, a gravity-driven flow, a pressure-generating pump, or an electroosmotic flow. Controlling the flow rate through the flow channels can be used to tailor the amount of assistance that the flow lends to the transport of the analyte zone to the detector electrodes.

Figure 7A:
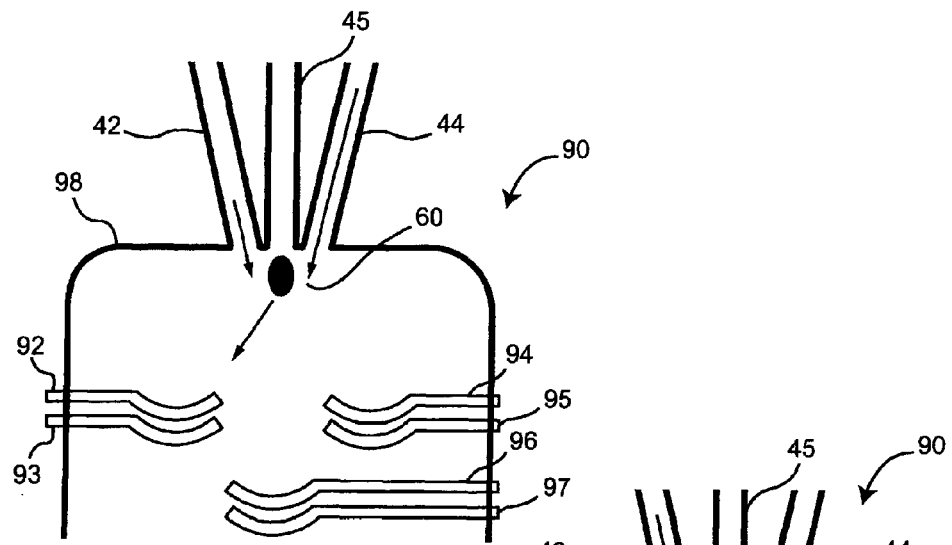
FIGS. 7A, 7B, and 7C are diagrammatic representations illustrating how the relative flow from the side channels of an EC detector of the present invention may be adjusted by altering the balance of the flow in the two side sheath channels.
Figure 7B:
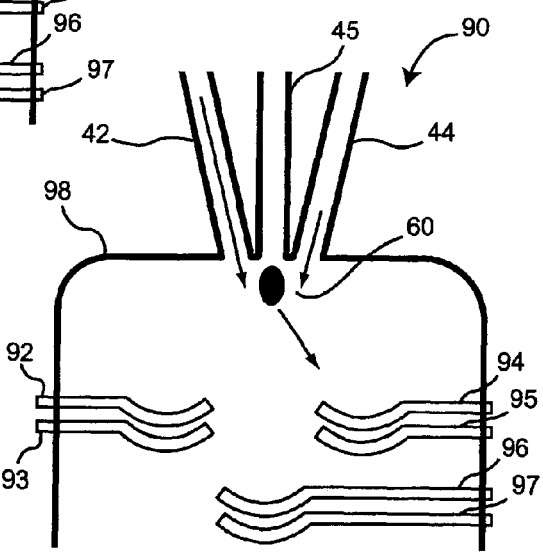
Figure 7C:
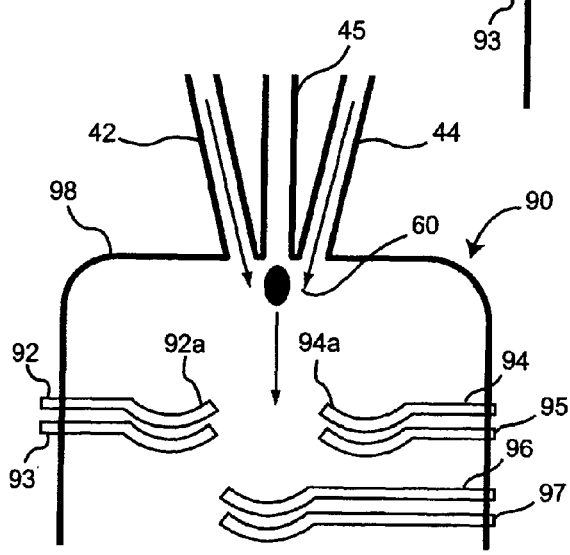

Additionally, the relative rate of the channel flows can be adjusted to steer the analyte zone 60 laterally to one side or the other in order to more accurately encounter single or multiple discreet electrodes of an EC detector. For instance, as shown in FIGS. 7A-7C, an EC detector 90 may include multiple pairs of working and reference electrodes, electrodes 92 and 93, 94 and 95, and 96 and 97, spatially separated in a way that adjusting the relative channel flows can be used to address individual pairs of working and reference electrodes. Each pair of electrodes could be identical, for example, for redundancy in case of the failure of a particular pair. Alternatively, they could be different, for example, posed at various potentials, or chemically modified such that they are selective for particular analytes and not selective for other analytes.

As shown in FIG. 7A, the flow from the channel 44 may be greater than that from the channel 42. As such, the analyte zone 60 is directed towards the working electrode 92 and the reference electrode 93. Conversely, as shown in FIG. 7B, the flow from the channel 42 may be greater than that from the channel 44. This directs the analyte zone 60 towards the working electrode 94 and the reference electrode 95. Also, as shown in FIG. 7C, the flow in the channels 42 and 44 may be approximately equal such that the analyte zone 60 is directed toward a midpoint between ends 92a and 94a of the electrodes 92 and 94, ultimately encountering the working electrode 96 and associated reference electrode 97.

Because the sheath flow system effectively decouples the transport of the analyte zone from the electrophoretic current, it may also be used to enable multiplex detection due directly to the high velocity, low-dispersion transport afforded by the sheath flow. By arraying multiple electrodes specific for different analytes, for example, by poising them at different potentials or by surface modification to make them selective for only a particular electroactive reagents along the direction of a confluent sheath flow, an analyte stream can be multiply interrogated.

Figure 8A:
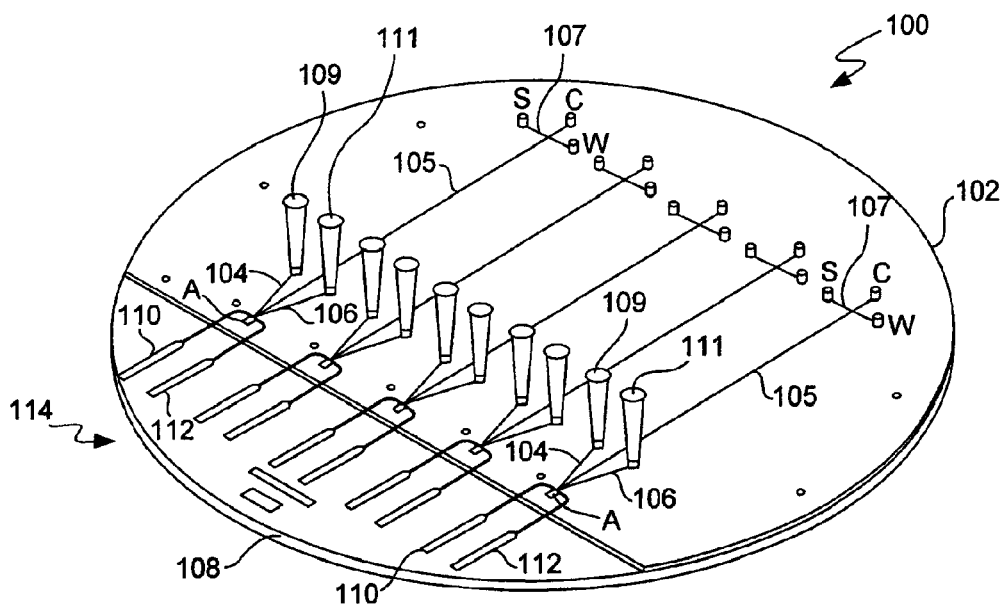
FIG. 8A is a diagrammatic representation of an assembled CE-EC separation and detection microfabricated system in accordance with the present invention.
Figure 8B:
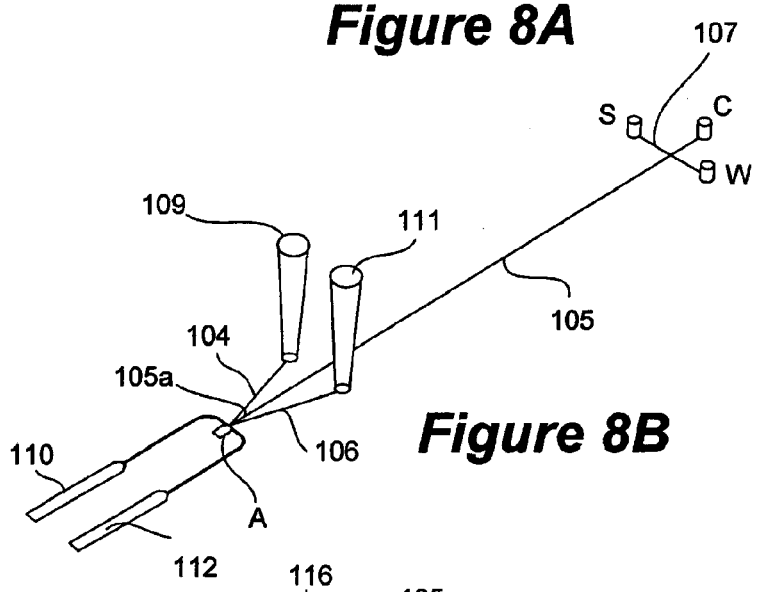
FIG. 8B is a diagrammatic representation depicting a single CE-EC device of FIG. 8A.

Microfabricated EC chips containing an integrated sheath-flow EC detector have been fabricated with the goal of minimizing the influence of separation voltages on end-column detection while maintaining optimum performance. As shown in FIGS. 8A and 8B, such a CE-EC microdevice or microfabricated system 100 comprises an upper glass wafer 102 forming a number of sample reservoirs (S), waste reservoirs (W), cathode reservoirs (C), and anode or detection reservoirs (A). The upper wafer also carries a number of etched sheath-flow channels 104 and 106, and associated etched separation channels 105. Additionally, the upper wafer carries etched injector channels 107 for the CE system. The CE-EC system 100 further includes a lower glass wafer 108 on which working and reference electrodes 110 and 112 of a microfabricated CE-EC system 114 have been fabricated.

A pair of sheath-flow channels 104 and 106 join an end of a separation channel 105 from each side, and the flow in the channels is gravity-driven from respective reservoirs 109 and 111. The flow in the channels carries an analyte to the electrodes 110 and 112. The detector electrodes may be placed at working distances, for example, 100, 150, 200 and 250-μm, from a separation channel exit 105a.

The performance of such a device was evaluated using the electroactive compound catechol and a detection limit of 4.1 μM (micron-molar) obtained at a working distance of 250 μm. Detection of DNA (deoxyribonucleic acid) restriction fragments and PCR (polymearse chain reaction) product sizing was demonstrated using the electroactive intercalating dye, iron phenanthroline. Additionally, an allele-specific PCR based single nucleotide polymorphism typing assay for the C282Y substitution diagnostic for hereditary hemochromatosis was developed and evaluated using ferrocene-labeled primers. This study illustrated the feasibility of high-speed, high-throughput chemical and genetic analysis using microchip EC detection.

More specifically, the CE-EC system 100 was formed by sandwiching upper and lower borosilicate glass substrates (D263, Schott, Yonkers, N.Y.) containing the etched fluidic elements and metallized electrodes, respectively. Each capillary had an effective separation length of 5 centimeters (cm) and was etched 15-μm deep and 60-μm wide. The injector was a twin-T design with a 250-μm offset. A pair of side or sheath flow channels 104 and 106, for example, 1-cm long by 60-μm wide, flanked each separation channel 105 and were joined to it just before the channel end 105a (see FIG. 8C). The separation channel may widen to approximately 1000×1500 μm after the convergence to form the detection reservoir (A). To minimize the effect of the CE electric field on electrochemical detection, the working electrodes were placed between 100 and 250 μm from the separation channel exit 105a. To further isolate the working and reference electrodes from EC currents, a passivating layer of silicon oxide was deposited on the platinum leads addressing each electrode.

The metallic elements of the EC detector were constructed on the lower glass wafer. These elements consisted of gold-plated working and silver-plated reference electrodes addressed by silicon oxide passivated platinum leads. First, the lower wafer was sputter-coated with a thin film of platinum (Pt) using titanium (Ti) as an adhesion layer to a total thickness of about 2000 angstroms (Å.) The gold working electrodes were formed by first coating the wafer with a thick resist (~10 μm, SJR-5740, Shipley) and exposing the pattern in a contact aligner. After developing and brief oxygen ($O_2$) plasma ashing, gold was electroplated up through the exposed areas in the photoresist using Pt as a seed layer. Electroplating was performed using a gold sulfate solution (Technic, San Jose, Calif.) and a constant current of 1 mA for 10 minutes (min). The electroplating formed 3.5-μm thick electrodes in all areas where the photoresist had been exposed. EC surface areas from 2183 to 3290 μm$^2$ were obtained despite similar plating heights of 3.5±0.4 μm. The remaining photoresist was stripped and the wafer was thoroughly cleaned using $O_2$ plasma ashing and a piranha solution. A 2000-Å thick passivating silicon oxide film was then deposited on the entire wafer by LPCVD. The silicon oxide film was patterned photolithographically and selectively removed by a 2 min etch in a buffered HF solution (1:5 HF:$NH_4F$). To form the silver reference electrodes, thick photoresist was applied and patterned as for the gold electrodes. The wafer was transferred to a silver plating solution (ACR 1006, Technic) and electroplating was performed for 15 min, resulting in a 5.0-μm silver layer. The photoresist was then stripped and the wafer was piranha-cleaned and ashed. Final patterning of the platinum leads used thick photoresist to mask the electrodes and an ion mill (Microetch, Veeco, Woodbury, N.Y.) to remove all platinum not covered by photoresist. The working and reference electrodes were patterned such that they were spaced 20-μm apart. The glass sandwich structure was completed by alignment of both wafers or substrates (MA6/BA6, Karl Suss) followed by thermal compression bonding at 560° C. for 3 hours.

After bonding, the electrodes were cleaned using the conventional RCA procedure (1:1:5 of conc. $NH_4OH$: 30% $H_2O_2$: $H_2O$ wash followed by 1:1:6 conc. HCl:30% $H_2O_2$: $H_2O$). Activation of the Ag/AgCl reference electrodes was achieved by oxidizing the silver electrode for 10 min in a 1 M NaCl solution. Investigation of electrochemical behavior and calculation of surface areas of all working electrodes were performed using 4 mM ferricyanide prior to usage. Pt leads were used to connect the chip to a potentiostat via a standard PC card-edge connector.

Catechol was used to characterize the sheath-flow and detector design by performing capillary zone electrophoresis (CZE) separations in uncoated channels. The separation channels were washed before each run using 1 M NaOH and dd$H_2O$, while electrodes were cleaned using the above mentioned RCA cleaning procedure (introduced through the sheath-flow channels). TAE (1×: 40 mM Tris-acetate, 1 mM EDTA, pH 8.2) containing 1 mM KCl was used as the EC buffer for all measurements except where noted. The catechol stock solution (10 mM) was prepared by dissolving catechol (Sigma, St Louis, Mo.) in 10 mM $HClO_4$. Samples were diluted to the desired concentrations in electrophoresis buffer and prepared fresh every day.

As outlined in FIGS. 8A and 8B, the high sheath-flow buffer reservoirs 109 and 111, which were approximately 2 cm high, were formed by inserting cutoff 200-μL pipette tips into drilled access holes. Each tip was filled with 150 μL of buffer (~15-mm head) which was sufficient to establish a constant gravity-driven flow through the sheath-flow channels and into the detection reservoir (A). This sheath flow was sufficient to increase the velocity of catechol by ~50 μm/s in the detection reservoir during CZE separations.

A sample was introduced by a pinched injection at 400 V/cm (volts per centimeter) for 30 seconds from the sample (S) to the waste (W) reservoir employing −200 V at injection, +200 V at waste, +50 V at the cathode reservoir (C) and 0 V (ground) at the detection reservoir. After the injection, the CE field was then switched to electrophorese the sample plug down the separation column at 185 V/cm (+1000 V at the cathode and 0 V (ground) at the detection reservoir). A back-biasing electric field was applied to both sample and waste reservoirs (each at +700 V).

Figure 8C:
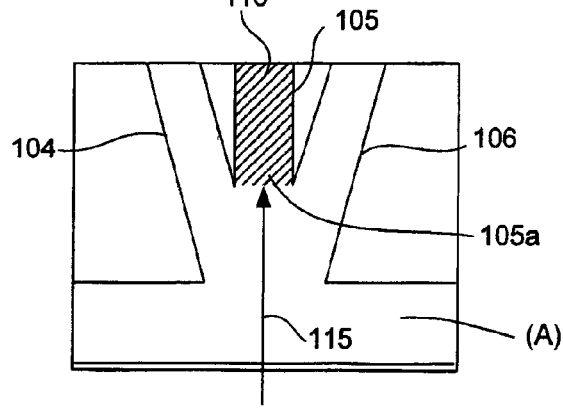
FIG. 8C is a diagrammatic representation depicting the location of a sieving matrix at the junction of the separation channel and the side channels of the CE-EC device of FIG. 8A.

DNA separations were performed on polyacrylamide-coated channels using a hydroxyethylcellulose (HEC) sieving matrix. Iron phenanthroline (Fe(1,10-phen)$_3^{2+}$, from Alfa Aesar), an intercalating redox-active dye, was diluted to 1 μM working concentration and added to the sieving matrix and electrophoresis buffer. The sieving matrix was degassed under vacuum for 10 min, centrifuged, and then loaded into the channel by syringe through the cathode reservoir. FIG. 8C illustrates the optimum position of a gel within the separation/sheath-flow junction, where the arrow 115 at the edge of the separation channel indicates the meniscus of the cellulose sieving matrix 116. HEC leakage into the sheath-flow channels and the detection reservoir can cause serious distortion of the CE separation. Excess sieving matrix could be cleared from these areas by flushing dd$H_2O$ through the sheath-flow channels. Inspection of the separation/sheath-flow junction was performed prior to each run. A BstN I digest of pBR322 DNA (New England Biolabs, Beverly, Mass.) was used as molecular weight standard and diluted to 100 ng/μL in 0.1× TAE. DNA samples (5 μL) were placed in the sample reservoirs while 10 μL of run buffer was placed in the waste, cathode and detection or anode reservoirs. Separation and detection of ferrocene-labeled primers and PCR products were performed in a similar manner, but in the absence of redox-active intercalator dyes.

EC detection was carried out amperometrically with a three-electrode potentiostat (LC-4C, Bioanalytical Systems, West Lafayette, Ind.) controlled by LabView software (National Instruments, Austin, Tex.), allowing manipulation of applied potential, sampling frequency, detection range and gain settings. The working electrode was maintained at +800 mV for catechol and +950 mV vs the internal Ag/AgCl reference electrode for DNA separations using intercalator dyes. The output signal from the detector was sampled at 30 Hz and filtered digitally to remove high-frequency noise. Data collection was initiated 5 seconds after application of the separation voltages, and steady state background conditions were rapidly established. A high-voltage power supply was used to drive electrophoresis. This unit was mounted inside a faradaic cage (30×30×30-cm wooden frame surrounded by copper mesh) to further reduce external noise levels.

Amino-modified (AmC6-at 5' end) allele-specific primers (see Table 1 below) were obtained from Operon and labeled as follows: First, a solution of ferrocenecarboxylic acid (1 mmol), N-hydroxysuccinimide (1.2 mmols), N,N-diisopropylethylamine (2.5 mmols) and dicyclohexylcarbodiimide (1.1 mmols) was dissolved in 10 mL THF and stirred under nitrogen at room temperature for 5 hours. The synthesis of N-hydroxysuccinimide ester of ferrocenecarboxylic acid was followed using TLC and the reaction was found to be complete after 5 hours. The precipitate formed during the reaction was filtered off while the filtrate was concentrated to dryness and the obtained solid was chromatographed on silica gel (Merck 60, chloroform eluent). The yellow fraction (87% yield of ferrocene-succinimide) was collected, dried and stored at −20° C. prior to use. The aminohexyl-linked oligonucleotides (10 nmol) were dissolved in 80 μL of 0.5 M NaHCO$_3$/NaCO$_3$ buffer (pH 9.0) and 20 μL of a dimethylsulfoxide solution (DMSO) containing 1 mmol of ferrocene-succinimide. The mixture was allowed to react at room temperature overnight and desalted using MicroSpin G-25 columns (Amersham Biosciences) prior to HPLC purification. Aminohexyl-linked oligonucleotides and ferrocenyl-oligonucleotides were purified to homogeneity by HPLC (Prostar, Varian, Walnut Creek, Calif.) at 25° C., flow rate 1 mL/min using a 0.1 M triethylammonium acetate (TEAA) buffer at pH 6.9 and an applied linear gradient of 10-30% acetonitrile within 30 min. The retention times of the unlabeled and labeled oligonucleotides were 12.1 min and 21.9 min, respectively. MALDI-TOF MS was use to confirm the successful conjugation of ferrocene (Fc) to the primers. The WTFWD primer (see Table 1) m/z ratio was 5923±5 (calculated m/z=5926) and the VTFWD primer m/z ratio was 5935±6 (calculated m/z=5940). Final Fc-labeled oligonucleotide concentrations were determined optically at 260 nm using the molar extinction coefficients $\epsilon_{260}$=166,893 cm$^{-1}$ and 168,237 cm$^{-1}$ for the WT and VT forward primers. Recovered ferrocenyl-oligonucleotides concentrations were calculated to be 4.2 and 4.5 nmols, thus resulting in a reaction yield of 42 and 45%. The lyophilized ferrocene-labeled oligonucleotides were stored at −20° C. prior to usage.

TABLE 1

Primer sequences used for PCR reactions

| Name | Sequence 5'-3' |
|---|---|
| WTFWD (Sequence Id. No. 1) | [AmC$_6$]-CTGGGTGCTCCACCTGGC Amino modified primer for 282C (wt) |
| VTFWD (Sequence Id. No. 2) | [AmC$_6$]-CTGGGTGCTCCACCTGGT Amino modified primer for 282Y (vt) |
| 232-RVD (Sequence Id. No. 3) | AAGGTGACACATCATGACC Reverse - 232 bp PCR product |
| FWD (Sequence Id. No. 4) | CCTACCAGGGCTGGATAACC Forward - 223 bp PCR product |
| RVD (Sequence Id. No. 5) | CTGGCTCTCATCAGTCACATA Reverse - 223 bp PCR product |

DNA from three individuals (CEPH, Coriell Cell Repository, Camden, N.J.) previously typed for C282Y variants was used to evaluate the detector performance. Genomic DNA samples consisted of a 46 year old male (NA 14620) typed homozygous Y/Y, a 47-year-old female (NA 14641) typed heterozygous C/Y as well as a female (NA 10859) homozygous for the wildtype C/C allele. Stock solutions of the genomic samples at 10 ng/μL were prepared in 10×TE buffer and stored at −20° C. PCR reaction volumes of 50 μL contained 25 μL Qiagen PCR HotStarTaq master mix, 50 ng genomic DNA and 0.5 μM primers. The reaction underwent an initial activation at 95° C. for 15 min, followed by 30 cycles consisting of annealing at 62° C. for 30, extension at 72° C. for 1 min and denaturation at 94° C. for 30 sec.

Allele-specific extension assays were carried out in 25 μL volumes containing Qiagen PCR HotStarTaq master mix, 50 ng genomic DNA and allele-specific reverse and ferrocene-labeled forward primers (0.5 μM). PCR was carried out on an MJ Research PTC-100 programmable thermal cycler (Watertown, Mass., USA) using a step-down protocol. Reactions underwent initial activation at 95° C. for 15 min, a denaturation step at 94° C. for 45 seconds, followed by annealing at 71° C. for 1 min and extension at 72° C. for 1 min. Annealing temperatures were dropped 1° C. for 5 subsequent cycles until 67° C. was reached and cycling was completed after 35 cycles had an annealing temperature of 66° C. for 1 min followed by a 4° C. hold. The presence of amplicons and PCR yield was verified using agarose slab gel electrophoresis.

The sheath-flow supported EC detection system is capable of active and localized transport of analytes from the separation channel exit to the working electrode. The sheath-flow channels, approximately 1-cm long, were placed at a 30° angle relative to the separation channel to focus the fluid stream over the middle of the working electrode. Based on the geometric focal point of the two fluid streams, calculated to be 300 μm inside the detection reservoir, the working electrode was placed at a maximum distance of 250 μm from the separation channel. The position of the reference electrode also has a pronounced effect on detector performance. It has also been shown that optimum detector performance is achieved when the relative spacing between both working and reference electrodes is less than the separation channel diameter. If the working and reference electrodes are positioned on an equipotential plane, variations in the CE high voltage will not alter the potential difference between the two electrodes, thereby eliminating additional charging currents, and decreasing background noise levels. The reference electrode was thus placed 20 μm behind the working electrode to minimize the influence of the CE voltage drop.

Initial CZE experiments were performed using non-plated (2000 Å thick) platinum working electrodes positioned 250 μm from the separation channel exit to evaluate the feasibility of the sheath-flow supported detector design. This study revealed flat baselines with separation voltages between 100 to 300 V/cm and a limit of detection for catechol of 20 μM which is a factor of 5 higher than has been previously reported. Electrodes with greater electrochemical surface area were expected to decrease detection limits and improve detector performance. Such electrodes were realized by electroplating gold onto the previously described working electrodes. Three different gold plating heights (2.5, 3.5 and 5 μm, respectively) were investigated, all of which resulted in significantly increased signal intensity versus the non-plated electrodes.

Figure 9:
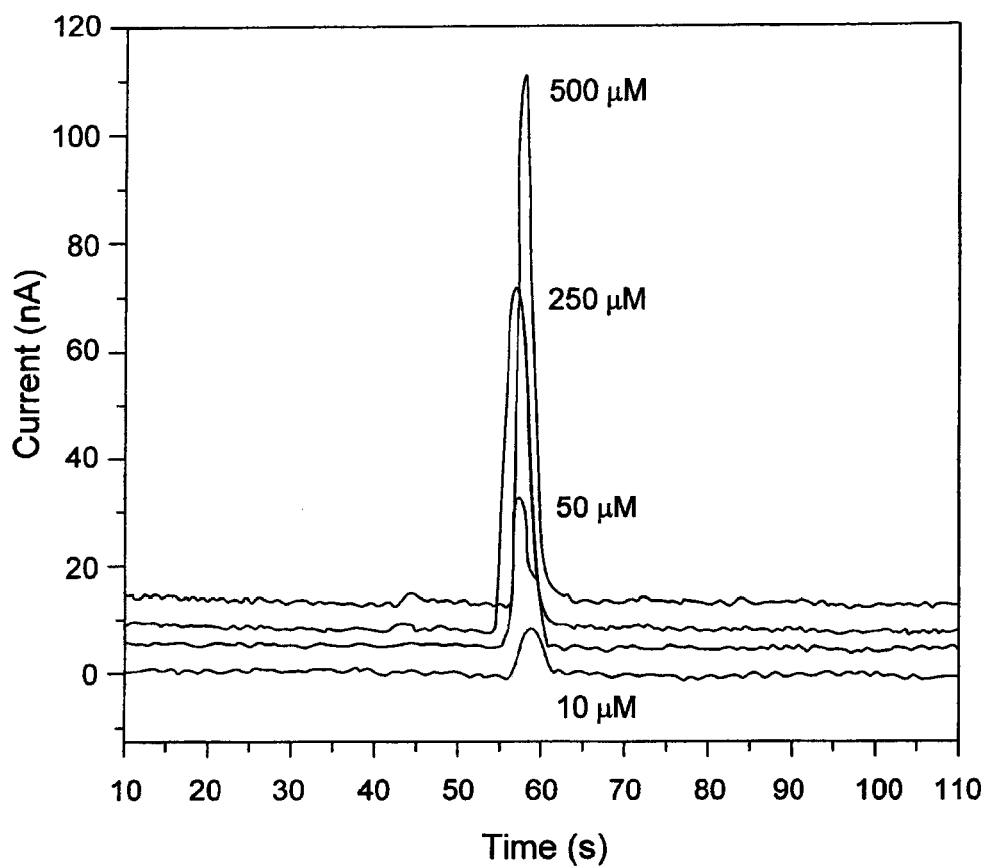
FIG. 9 is a graphical representation of electropherograms (current versus time) for different concentrations of an electroactive compound undergoing capillary zone electrophoresis in a CE-EC system in accordance with the present invention.

FIG. 9 presents electropherograms obtained for decreasing concentrations of catechol (500, 250, 50, and 10 μM) using the 3.5-μm high plated gold working electrodes. Separations were performed at 200 V/cm in 1×TAE containing 1 mM KCl with an applied EC otential of +800 mV. The response for catechol was found to be linear between 10 and 500 μM with an average migration time of 55 seconds. Decreasing analyte concentrations also resulted in decreased background current. Only a small increase in signal intensity (about 20%) was observed when electrode heights were increased from 2.5 to 5 μm. Unless otherwise stated, all subsequent electrophoresis measurements were performed using a 3.5-μm high gold plated working and 5-μm high silver reference electrode.

To further characterize the sheath-flow EC detector, the impact of two different working electrode distances (150 and 250 μm from the separation channel exit) were examined. Separations were performed at 200 V/cm in 1×TAE containing 1 mM KCl with an applied EC potential of +800 mV. In both cases, a linear response to catechol between 10 and 1000 μM was observed with sensitivities of 0.21 and 0.18 nA/μM and detection limits of 3.8 and 4.1 μM (linear fits gave intercepts and $R^2$ values of 4.4 and 0.998; and 2.4 and 0.996, respectively). Limits of detection were based on the average response obtained with 10 μM catechol (N=6) at a S/N=3. Gold-plated working electrodes maintained low background noise levels while showing a 5-fold improvement in detector performance over the flat platinum electrodes.

To assess the characteristics of the sheath-flow EC detector in more detail, various concentrations of catechol were used to perform CE separations in the presence and absence of sheath-flow support. In all cases, significantly lower (about 90%) and broader signal peaks were obtained in the absence of sheath-flow support using both working electrode distances (150 and 250-μm). For example, at a working electrode distance of 250 μm from the separation channel exit, no signal was observed for a catechol concentration of 25 μM in the absence of sheath-flow support. Apparent elution times were also 3-4 seconds shorter with sheath-flow support.

Figure 10:
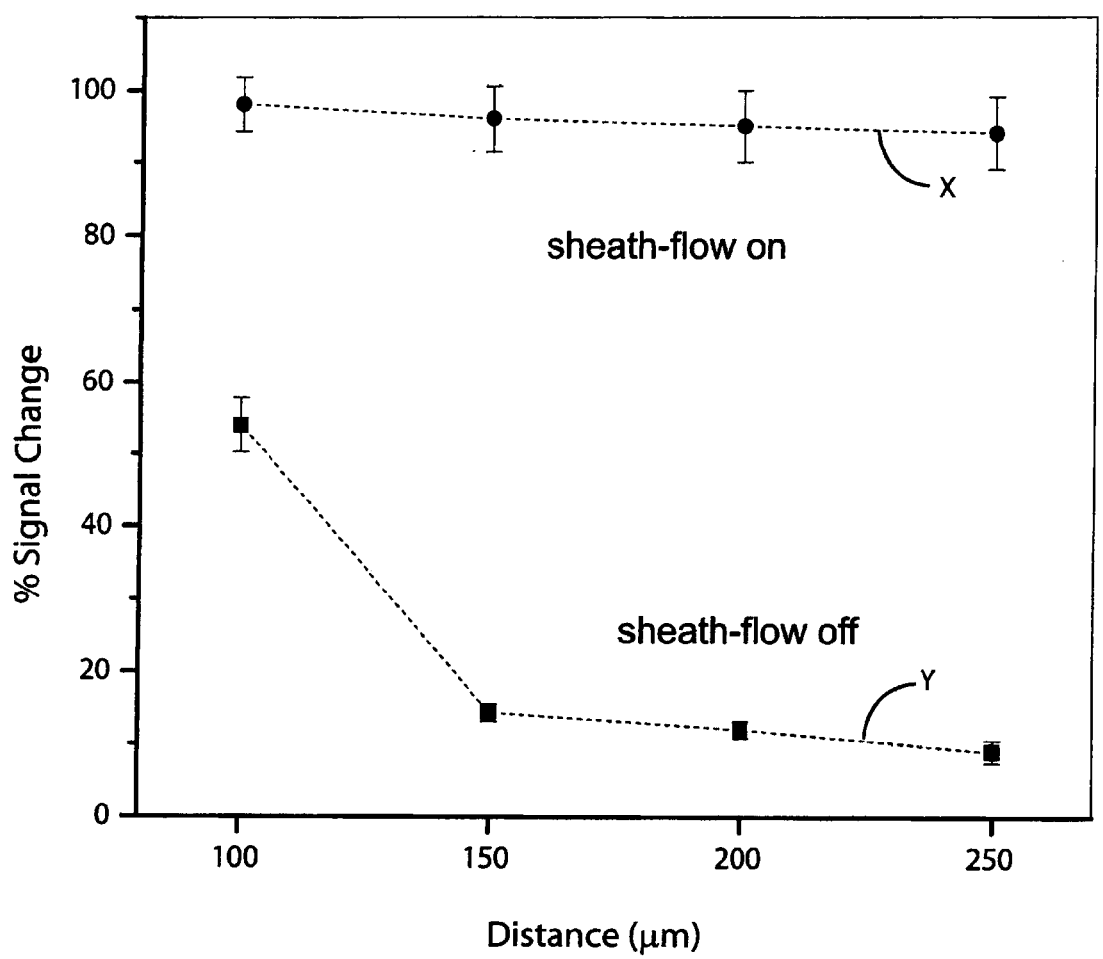
FIG. 10 is a graphical representation of the change in signal intensity versus the distance that a working electrode of an EC detector of the present invention is spaced from the end of a separation channel of a CE apparatus.

The impact of electrode distances on EC-detection was explored by fabricating four microchip CE-EC devices with electrochemical detectors positioned at a distance of 100, 150, 200 and 250 μm from the separation channel exit. CE-measurements were performed with (curve X) and without (curve Y) sheath-flow supported EC-detection using various concentrations of catechol (see FIG. 10). Only a small variation in signal intensity was observed for all spacings of the sheath-flow EC detection. In the absence of the sheath-flow, a 74% decrease in signal was observed between 100 and 150 µm, followed by further declines at 200 µm and 250 µm. This decrease in signal and concomitant increase in retention time and peak width is a direct function of the large reduction in velocity due to the decrease in electric field in the detection reservoir. The increase in diffusive broadening with increased retention time is compounded by the lack of a sieving matrix in the detection chamber. An increase in retention times by 3.2 to 4.8 seconds for electrode distances of 150 and 250 µm respectively was observed.

Table 2 (see below) summarizes results of this study. Chronoamperometric measurements of the electrochemical surface area were conducted after filling the detection reservoir with 4 mM ferrocyanide and electrochemical surface areas were calculated using the Cottrell equation for planar electrodes. These differences in working electrode ($E_w$) areas did not cause significant variations in signal intensities.

configuration which should produce no cross-talk between electrodes. Other CE-EC designs may include various working electrodes and materials, such as copper and gold, which can be operated at different applied potentials and distances under similar conditions. Such an advanced detection system should be able to differentially detect multiple analytes simultaneously and could ultimately be used for DNA-sequencing by using a four-nucleotide ladder containing different electroactive labels.

Figure 12:
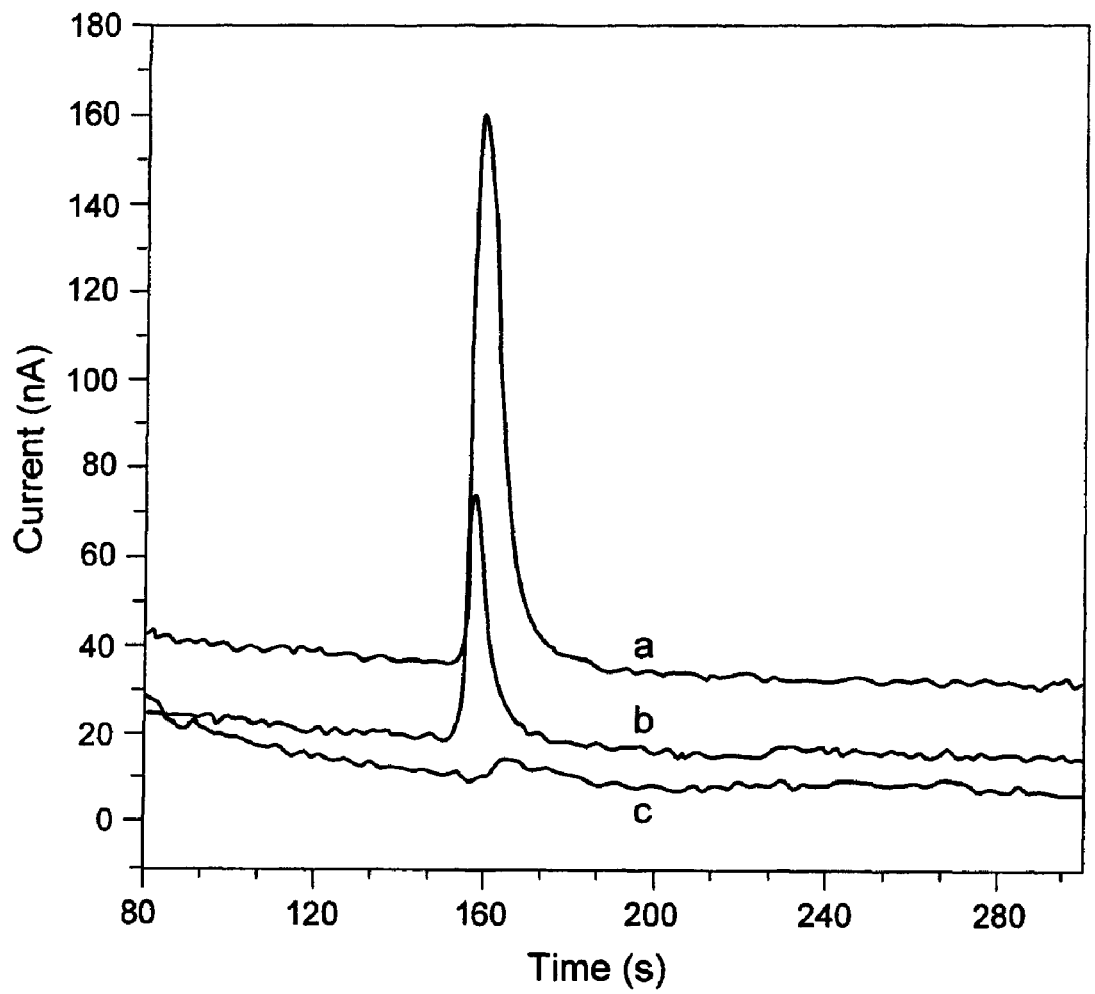
FIG. 12 is a graphical representation of electropherograms (current versus time) for different concentrations of ferrocene labeled single-strand DNA primers.

To explore the concept of multiplex electrochemical detection, the initial study used a redox-active ssDNA (single-strand DNA) probe created by linking ferrocene with a 5'-aminohexyl terminated primer. Ferrocenylated oligonucleotides have been widely used to detect DNA through hybridization and exhibit well characterized electrochemical properties. FIG. 12 presents electropherograms obtained from separations of decreasing concentrations of ferrocene-la-

TABLE 2

Sheath flow results vs. working distance

| $E_w$ distance | $E_w$ area | catechol conc. | * signal with sheath flow on | * signal with sheath flow off | remaining % | difference $\Delta t_r$ |
|---|---|---|---|---|---|---|
| 100 µm | 2650 µm² | 1000 µM | 184 nA | 112 nA | 61 | 3.2 ± 0.5 |
| 100 µm | 2450 | 400 | 73 | 35 | 48 | 3.1 ± 0.7 |
| 150 µm | 3290 | 500 | 89 | 14 | 16 | 3.3 ± 0.8 |
| 150 µm | 2890 | 250 | 51 | 6 | 12 | 4.5 ± 0.7 |
| 200 µm | 2824 | 250 | 48 | 7 | 14 | 4.5 ± 0.4 |
| 250 µm | 2583 | 600 | 124 | 11 | 8 | 4.3 ± 0.6 |
| 250 µm | 2183 | 100 | 24 | 5 | 7 | 4.8 ± 0.9 |

* Average of 3 replicate measurements and a RSD < 10%

Figure 11:
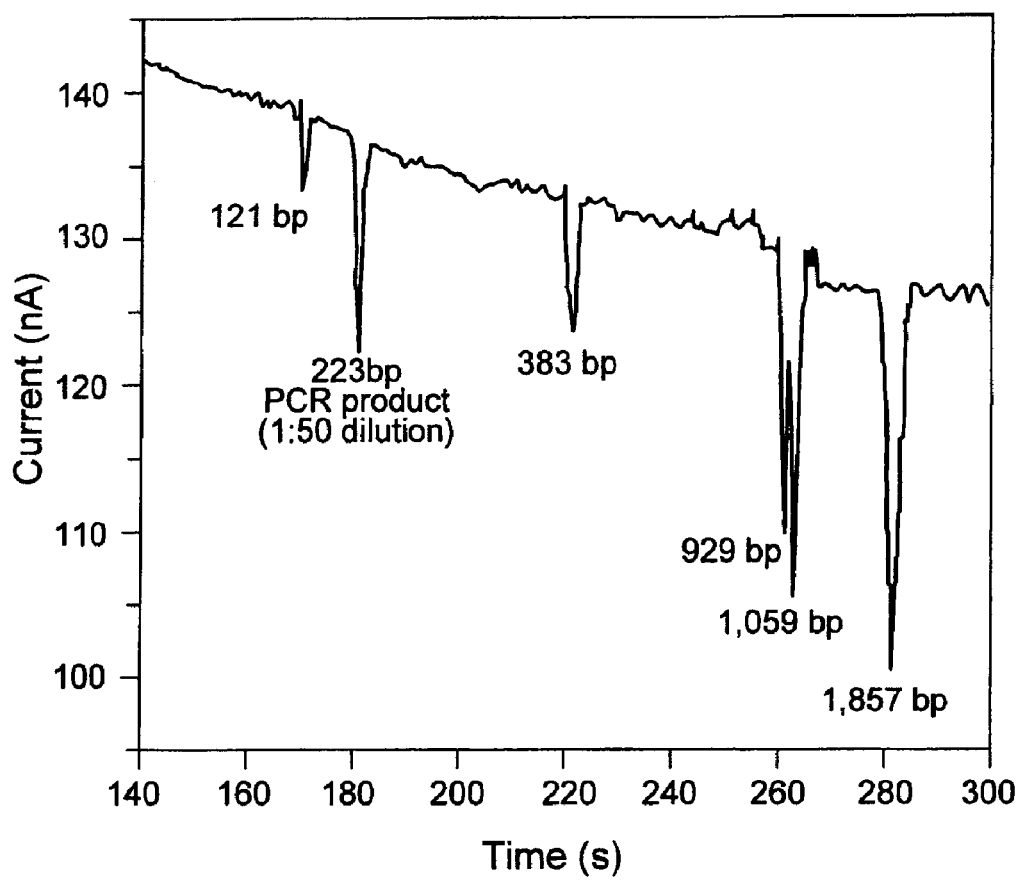
FIG. 11 is a graphical representation of an electropherogram (current versus time) of a capillary gel electrophoretic DNA analysis performed with an EC detector of the present invention.

A size-based gel electrophoretic separation of DNA using the sheath-flow EC detector was also performed. Initial measurements were based on indirect DNA detection using the redox-active intercalator dye iron phenanthroline (Fe(phen)$_3^{2+}$), which has been successfully applied to the detection of PCR products and DNA fragment sizing. With this technique, initial high background currents were obtained from free Fe(phen)$_3^{2+}$ in the separation and sheath-flow buffers. When complexed, DNA-Fe(phen)$_3^{2+}$ migrates past the detector and transient reductions in the background current are observed, indicating the presence of double-stranded DNA. The electrodes employed for this work were placed 150 µm from the separation channel exit. Care was taken to avoid leakage of the sieving matrix into the separation/sheath-flow junction as it seriously distorted peak shapes or dramatically decreased the measured signal. Additionally, residual gel deposits at the working electrode were found to block DNA-detection. No measurable signals were obtained when the separation channel was not completely filled with gel. DNA fragment sizing was demonstrated using a 1:50 dilution of a 223-bp PCR product mixed with a BstN I digest of pBR 322 (100 ng/µL) as a size standard. Separations were performed at 200 V/cm in 1×TAE buffer with 1 mM KCl containing 1-µM Fe(phen)$_3^{2+}$ with an applied EC potential of +950 mV (see FIG. 11). Although relatively high concentrations of DNA digest and PCR product were needed to detect DNA fragments, the result clearly demonstrates the feasibility of the sheath-flow supported electrochemical detector for DNA fragment sizing.

These results are important because the 150-µm distance from the separation channel exit to the working electrode eliminates interfering effects of the CE potential, and also leaves room for the implementation of multiple working electrodes, while maintaining a spatially well-defined electrode beled primers (60 (curve a), 30 (curve b) and 0.5 (curve c) µM) through 0.75% w/v HEC using the sheath-flow detector. The working electrode of the detector was located 150 µm from the separation channel exit. The response of the ferrocene-labeled oligonucleotides was found to be linear between 1 and 100 µM with an average retention time of 153.5±4.3 sec. The signal intensity of 3.8±0.6 nA (n=3) for 500 nM Fc-labeled primers was also deemed sufficient to analyze samples amplified by PCR. Separations were conducted at 200 V/cm with an applied EC potential of +750 mV.

Figure 13:
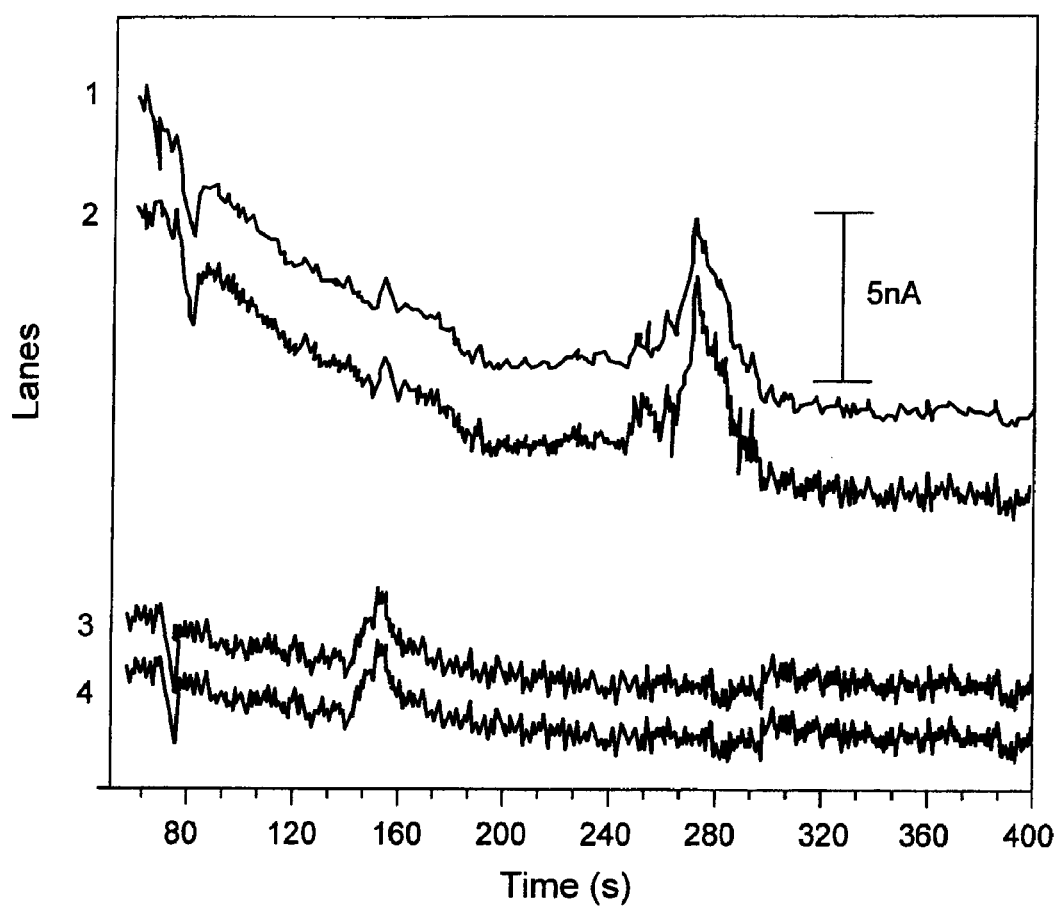
FIG. 13 is a graphical representation of electropherograms (lanes versus time) obtained with variant and wild type forward-primers for allele-specific extension assays from an individual homozygous for the variant 282Y-allele of the human HFE gene.

The sheath-flow EC detector was thus used to detect a SNP (single nucleotide polymorphisms) target using an allele-specific extension assay that employed Fc-labeled forward primers specific to each allele. After PCR amplification, the 5 µL samples were transferred into the four sample ports of the CE-EC device and separated. Separations were conducted at 200 V/cm with an applied EC potential of +750 mV. FIG. 13 presents the results from an individual homozygous for the 282Y variant allele of the human HFE gene. The electropherograms clearly show the presence of the variant amplicon (upper lanes: 1, 2) and absence of the wild type amplicon (lower lanes: 3, 4). Analyses of the remaining samples showed complete agreement with the reference method (data not shown). The removal of excess contaminating reagents (primers, salt, enzyme and dNTPs) was not necessary prior to each run, greatly simplifying the assay. The successful detection of redox-active labeled primers and PCR amplicons under less than optimal conditions clearly illustrates the power of the sheath-flow supported detector design for SNP genotyping.

A microfabricated sheath-flow EC detector that controls and minimizes interference from EC potentials has been described. The precise control of critical electrode characteristics, such as shape, size and orientation, on a microchip makes microfabrication an attractive tool for the development of EC detection systems. The detector configuration was characterized utilizing catechol and comparable analytical performance was observed placing the electrode up to 250 μm from the separation channel exit. The fabrication of isolated gold and silver-plated electrodes placed deep within the detection reservoir resulted in improved detection efficiencies and low background noise levels. DNA fragment sizing was demonstrated using the redox-active intercalator dye iron phenanthroline. SNP genotyping using allele-specific PCR was successfully accomplished using specific ferrocene-labeled primers. This sheath-flow supported CE-EC system permits the use of multiple electrode systems capable of analyzing complex analyte mixtures, and truly portable microfluidic device and micro-total analysis systems (μTAS).

While the invention has been particularly shown and described with reference to specific embodiments, it will also be understood by those skilled in the art that changes in the form and details of the disclosed embodiments may be made without departing from the spirit or scope of the invention. For example, the embodiments described above may be implemented using a variety of materials. Therefore, the scope of the invention should be determined with reference to the appended claims.

What is claimed is:

1. An electrochemical detector comprising:
   a first working electrode and a reference electrode located in a detection reservoir, the detection reservoir in fluid communication with an exit end of a separation channel of a sample component separation apparatus, the first working electrode and the reference electrode being located at a distance downstream from the exit end of the separation channel;
   a first channel located on a first side of the separation channel and in fluid communication with the exit end of the separation channel;
   a second channel located on a second side of the separation channel and in fluid communication with the exit end of the separation channel; and
   the first and second channels configured and arranged to intersect with the detection reservoir at the exit end of the separation channel to provide a sheath flow at the juncture of the first and second channels at the exit end of the separation channel such that the sheath flow transports a sample component from the exit end of the separation channel without substantial dilution to the first working electrode.

2. The detector of claim 1 wherein the separation channel is configured to perform an electrophoretic separation.

3. The detector of claim 1 wherein the first side is one lateral side of the separation channel and the second side is an opposite lateral side of the separation channel.

4. The detector of claim 1 wherein the first side is an upper surface of the separation channel and the second side is a lower surface of the separation channel.

5. The detector of claim 3 or 4 wherein the first and second channels are arranged at an angle greater than 0° but less than or equal to 90° relative to the separation channel.

6. The detector of claim 4 wherein the first and second channels are configured and arranged such that a flow therethrough controls the lateral and vertical direction of movement of the sample component exiting the separation channel.

7. The detector of claim 1 wherein a fluid is introduced into the first and second channels by a gravity driven flow, a pressure-generating pump driven flow, or an electroosmotic driven flow.

8. The detector of claim 1 further including a first reservoir for introducing a fluid into the first channel and a second reservoir for introducing a fluid into the second channel.

9. The detector of claim 1 wherein the first and second channels are configured and arranged such that a flow therethrough is varied to direct the sample component to regions near the working electrode as it exits the separation channel.

10. The detector of claim 1 wherein the first working electrode is located at a distance of between about 100 and 250 microns from the exit end of the separation channel.

11. The detector of claim 1 wherein the first and second channels provide for the hydrodynamic transport of the sample component to the first working electrode.

12. The detector of claim 1 wherein the detection reservoir further includes a third electrode configured to function either as a working electrode or a reference electrode.

13. The detector of claim 1 wherein the detection reservoir further includes a second working electrode to detect a sample component that is different from that detected by the first working electrode.

14. The detector of claim 1 wherein the detection reservoir further includes a second working electrode poised at a different potential from that of the first working electrode.

15. The detector of claim 14 wherein the first working electrode is configured to detect a first electroactive agent and the second working electrode is configured to detect a second electroactive agent that is different from the first electroactive agent.

16. The detector of claim 1 wherein the first working electrode is spaced from the reference electrode by a distance that is less than a diameter of the separation channel.

17. The detector of claim 1 wherein the first and second channels extend substantially parallel to the separation channel and are fluidically connected to another channel that directs a fluidic stream over a working electrode.

18. The detector of claim 1 wherein the first and second channels are configured and arranged to control the lateral direction of movement of the sample component exiting the separation channel.

19. An electrochemical detector comprising:
   a working electrode and a reference electrode located in a detection reservoir, the detection reservoir in fluid communication with an exit end of a separation channel of a sample component separation apparatus, the first working electrode and the reference electrode being located at a distance downstream from the exit end of the separation channel;
   first and second channel means disposed at and in fluid communication with the exit end of the separation channel for providing a sheath-flow at the juncture of the first and second channels at the exit end of the separation channel such that the sheath flow transports a sample component to the working electrode without substantial dilution.

20. A sample component separation and detector apparatus comprising:
   a cathode reservoir;
   an anode reservoir;
   a working electrode and a reference electrode located in the anode reservoir;
   a separation channel having an exit end, and that defines between the cathode reservoir and the anode reservoir a sample transport path, said exit end in fluid communication with the anode reservoir, the working electrode and the reference electrode being located a distance downstream of said exit end;

a first channel located on a first side of the separation channel, and an output end of the first channel disposed at and in fluid communication with the separation channel at said exit end;

a second channel located on a second side of the separation channel, and an output end of the second channel disposed at and in fluid communication with the separation channel at said exit end; and the first and second channels configured and arranged to provide a sheath flow at the juncture of the first and second channels at said exit end such that the sheath flow guides an analyte from said exit end to the working electrode without substantial dilution.

21. The apparatus of claim 20 wherein the separation channel is configured to perform an electrophoretic separation.

22. The apparatus of claim 20 further comprising a plurality of separation channels and associated first and second channels, each separation channel defining, between an associated cathode reservoir and an associated anode reservoir, a sample transport path.

23. The apparatus of claim 20 wherein the sample component separation and detector apparatus is microfabricated.

24. The apparatus of claim 20 further including;

a sample reservoir coupled to the separation channel; and a waste reservoir coupled to the separation channel.

25. A method of detecting and separating a sample by electrophoresis comprising:

depositing a sample into a sample reservoir;

injecting a portion of the sample into a separation channel;

applying a voltage between a cathode reservoir and an anode reservoir so as to drive the sample portion along the separation channel toward an exit end of the separation channel; and providing a sheath flow at the exit end of the separation channel such that the sheath flow transports the sample portion, without substantial dilution, from the exit end of the separation channel to a working electrode located in the anode reservoir at a distance and spaced from the exit end of the separation channel.

26. The method of claim 25 further including providing control over the lateral and vertical direction of movement of the sample portion as it leaves the exit end of the separation channel.

27. The method of claim 25 further including controlling the sheath flow to steer the sample portion in a selected direction to the working electrode.

28. The method of claim 25 further including controlling the flow rate of the sheath flow.

29. The method of claim 25 further including providing control over the lateral direction of movement of the sample portion as it leaves the exit end of the separation channel to direct the sample portion to the working electrode.

* * * * *

UNITED STATES PATENT AND TRADEMARK OFFICE
CERTIFICATE OF CORRECTION

PATENT NO. : 7,438,792 B2
APPLICATION NO. : 11/107295
DATED : October 21, 2008
INVENTOR(S) : Richard A. Mathies et al.

It is certified that error appears in the above-identified patent and that said Letters Patent is hereby corrected as shown below:

In the specification

Column 1, line 18, STATEMENT REGARDING FEDERALLY SPONSORED RESEARCH, please change "The techniques and mechanisms of the present invention were made with Government support under NIH Grant No. HG01399 and Department of Energy Grant No. FG03-91ER61125" to -- This invention was made with government support under HG001399 awarded by the National Institutes of Health and with government support under DE-FG03-91ER61125 awarded by the U.S. Department of Energy. The government has certain rights in the invention. --.

Signed and Sealed this
Twenty-sixth Day of April, 2016

Michelle K. Lee
*Director of the United States Patent and Trademark Office*